(12) United States Patent
Mayer

(10) Patent No.: US 6,626,892 B1
(45) Date of Patent: Sep. 30, 2003

(54) MEDICAL INSTRUMENT

(76) Inventor: Paul Mayer, 6290 SW. 92$^{nd}$ St., Miami, FL (US) 33156

( * ) Notice: Subject to any disclaimer, the term of this patent is extended or adjusted under 35 U.S.C. 154(b) by 0 days.

(21) Appl. No.: 10/023,766

(22) Filed: Dec. 21, 2001

(51) Int. Cl.$^7$ .............................................. A61B 17/00
(52) U.S. Cl. ........................................ 606/1; 128/897
(58) Field of Search ................................ 600/210, 211, 600/213, 214, 215, 216, 217, 226, 227, 228, 229, 230, 231, 232, 233, 234, 235, 37, 16, 17, 18; 606/130, 148, 1; 128/897; 604/174

(56) References Cited

U.S. PATENT DOCUMENTS

| | | | |
|---|---|---|---|
| 5,279,575 A | * | 1/1994 | Sugarbaker ................ 604/174 |
| 5,871,017 A | | 2/1999 | Mayer |
| 5,928,138 A | * | 7/1999 | Knight et al. .............. 600/201 |
| 6,077,278 A | | 6/2000 | Mayer |
| 6,126,651 A | | 10/2000 | Mayer |
| 6,162,173 A | * | 12/2000 | Chin et al. ................. 600/235 |
| 6,221,083 B1 | | 4/2001 | Mayer |

* cited by examiner

Primary Examiner—Cary E. O'Connor
(74) Attorney, Agent, or Firm—Browdy and Neimark, P.L.L.C.

(57) ABSTRACT

A medical instrument for performing a procedure on body tissue, including: an elongated tool carrier member having a distal end; an operating tool mounted at the distal end; an operating mechanism coupled to the carrier member and the tool for allowing manual operation of the tool; and a stabilizing member carried by the carrier member and including a plate element disposed to bear against the body tissue in order to cause the tool to follow movement of the body tissue.

A method for performing a procedure on a body organ that is moving using the medical instrument describe above, by: positioning the instrument so that the plate element of the stabilizing member contacts the organ at a location where the procedure is to be performed; and manually manipulating the operating means in order to perform the procedure while maintaining the plate element of the stabilizing member in contact with the organ.

11 Claims, 7 Drawing Sheets

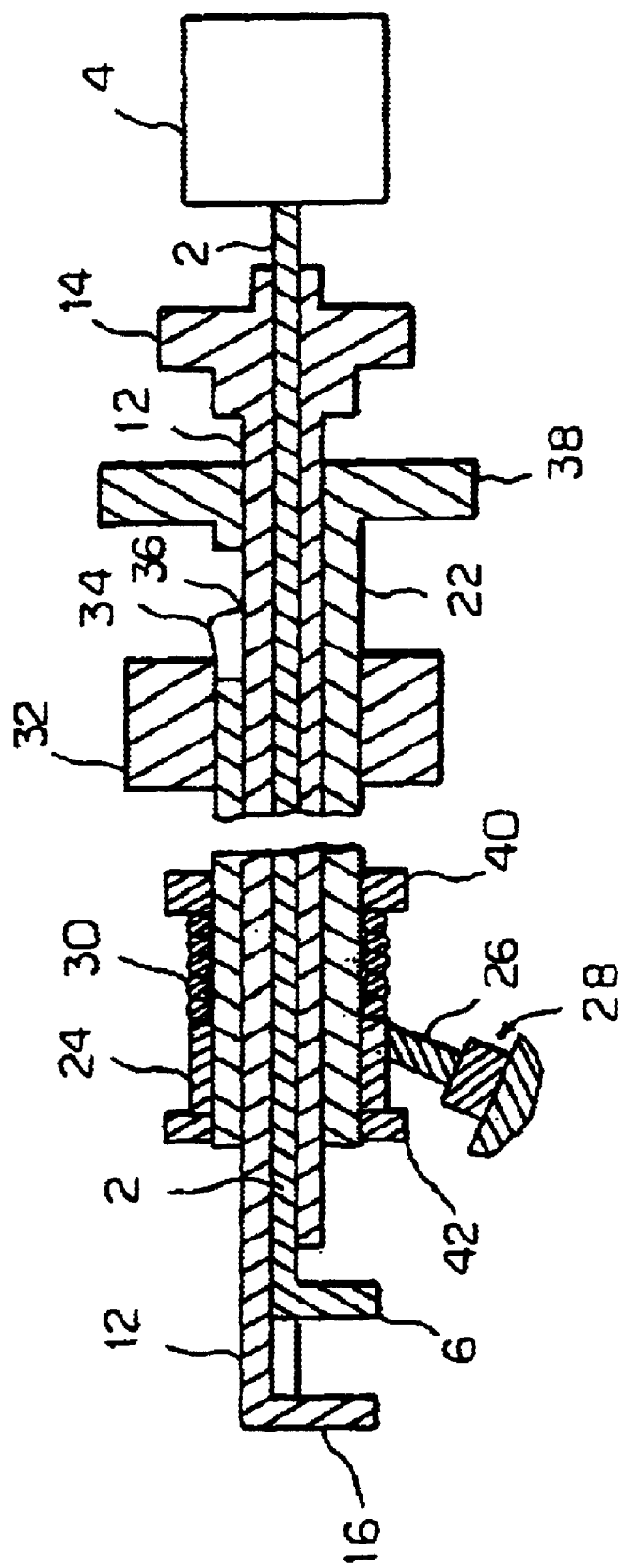

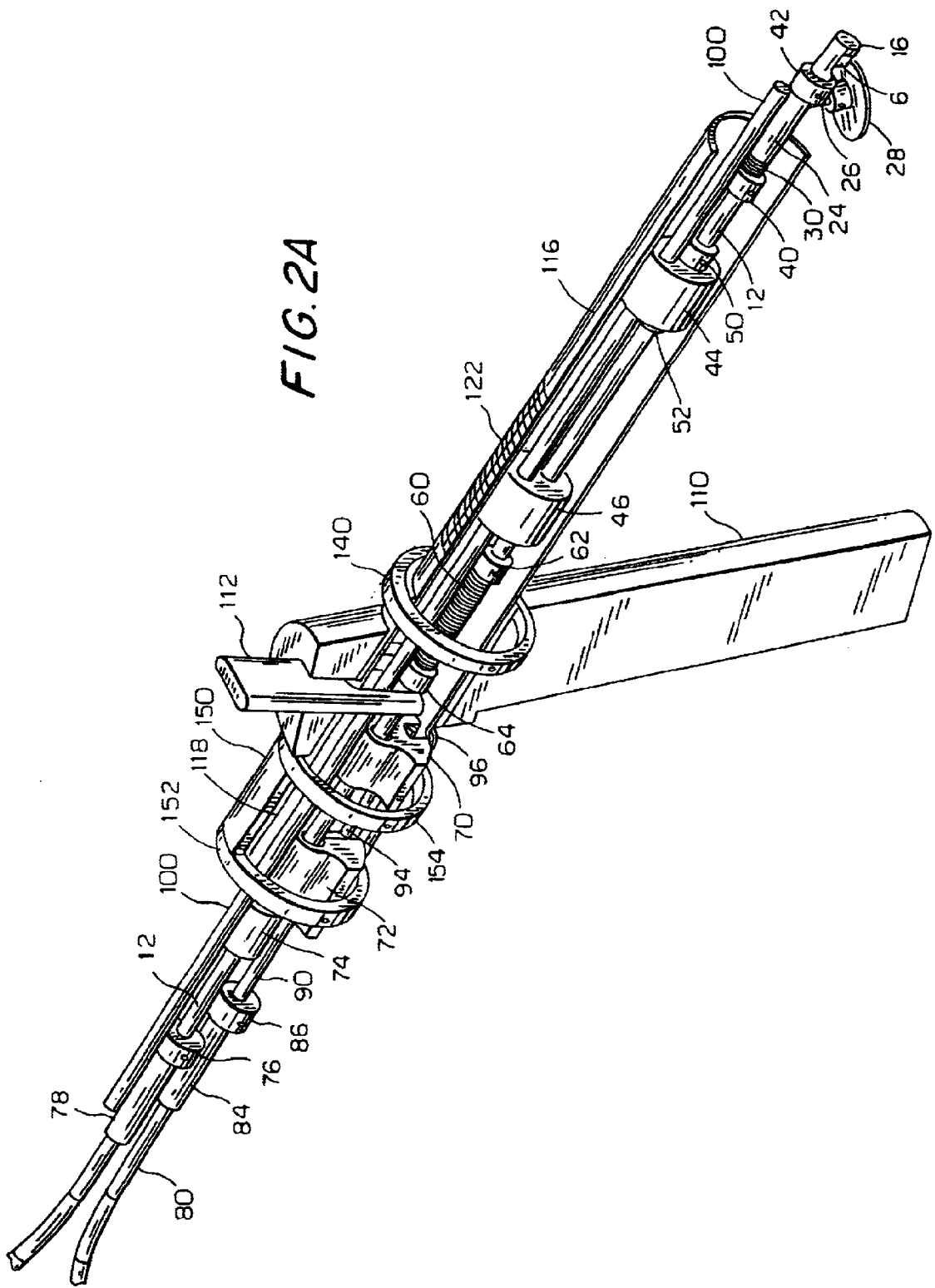

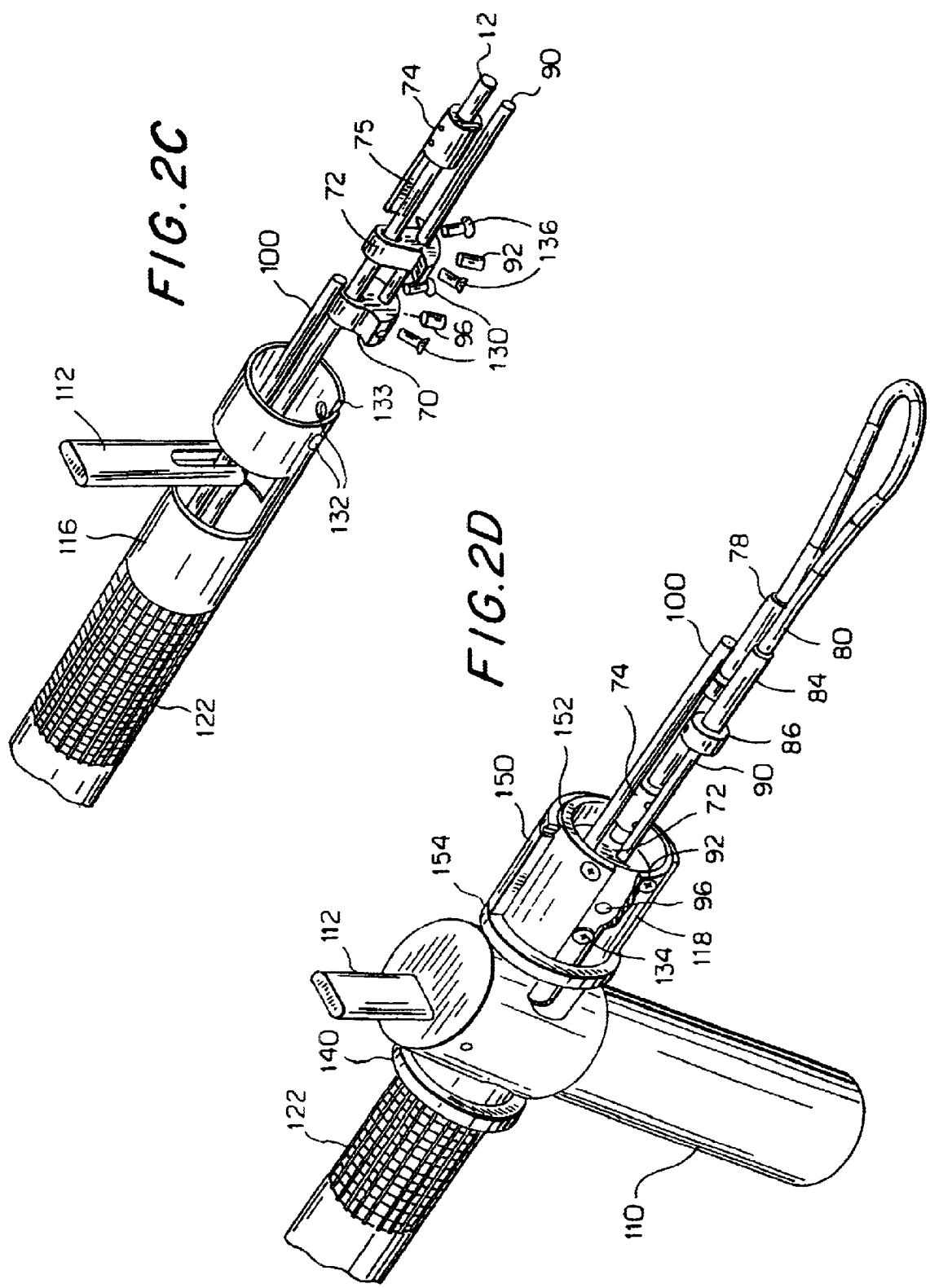

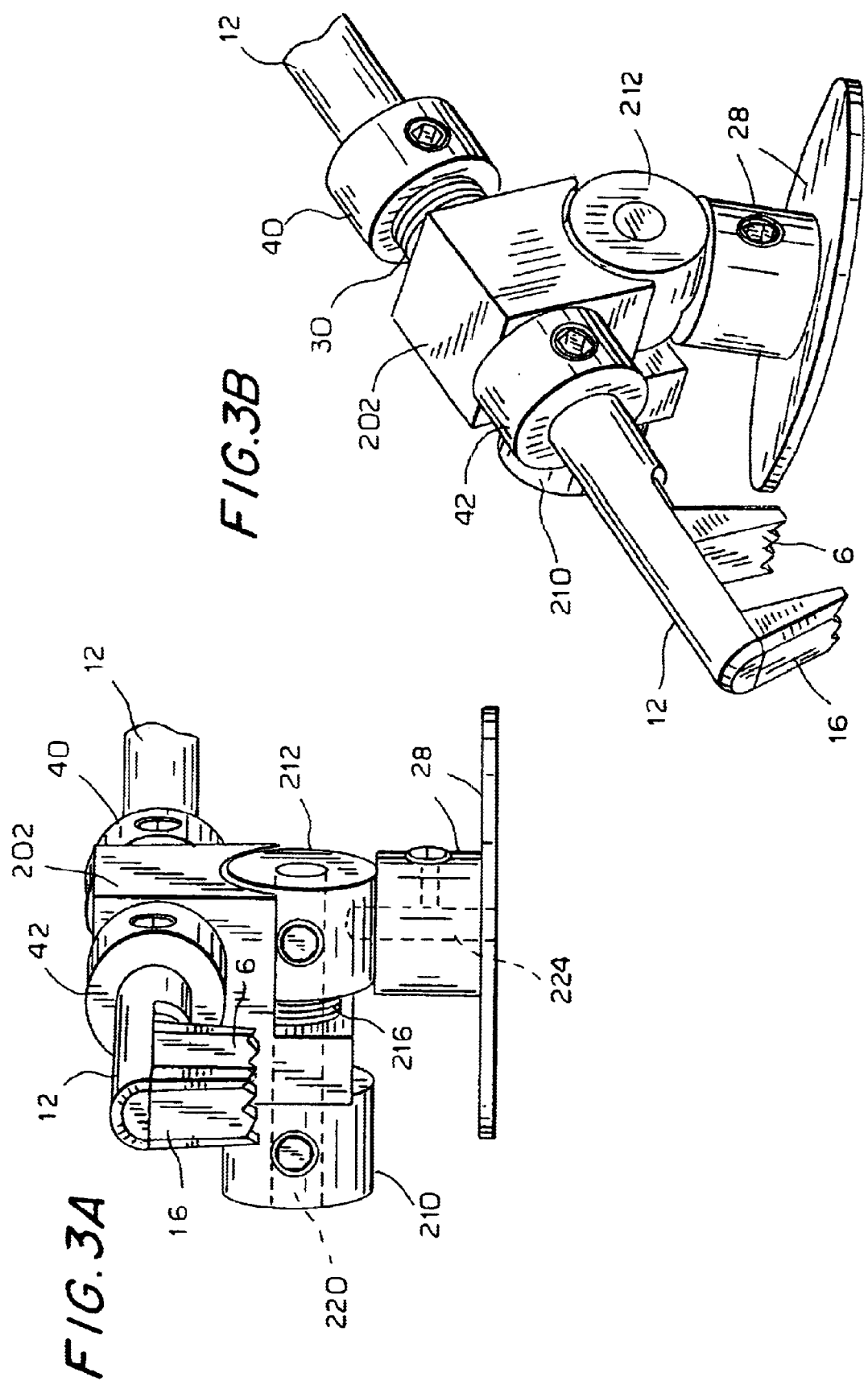

MEDICAL INSTRUMENT

BACKGROUND OF THE INVENTION

The present invention relates to medical instruments, and is particularly concerned with improved hand-held instruments for use in surgery.

BRIEF SUMMARY OF THE INVENTION

The present invention provides an approved medical instrument for performing a procedure on body tissue, and particularly on an organ that is in movement during the procedure.

To achieve this goal, the present invention provides a medical instrument for performing a procedure on body tissue, comprising:

an elongated tool carrier member having a distal end;

an operating tool mounted at the distal end;

operating means coupled to the carrier member and the tool for allowing manual operation of the tool; and a stabilizing member carried by the carrier member and including a plate element disposed to bear against the body tissue in order to cause said tool to follow movement of the body tissue.

The present invention further provides a method for performing a procedure on a body organ that is moving, using the above-described instrument. This method includes: positioning the instrument so that the plate element of the stabilizing member contacts the organ at a location where the procedure is to be performed; and manually manipulating the operating means in order to perform the procedure while maintaining the plate element of the stabilizing member in contact with the organ.

BRIEF DESCRIPTION OF THE DRAWING

FIG. 1B is an elevational, cross-sectional view of the first embodiment.

FIG. 2A is a first perspective view of a second embodiment of a medical instrument according to the invention.

FIG. 2C is a third perspective view, partly exploded and with certain components remove, of a portion of the second embodiment.

FIG. 2D is a fourth perspective view of a portion of the second embodiment.

FIGS. 3A and 3B are two perspective views of a modified form of construction of a portion of a medical instrument according to the invention.

DETAILED DESCRIPTION OF THE INVENTION

Figure 1A:
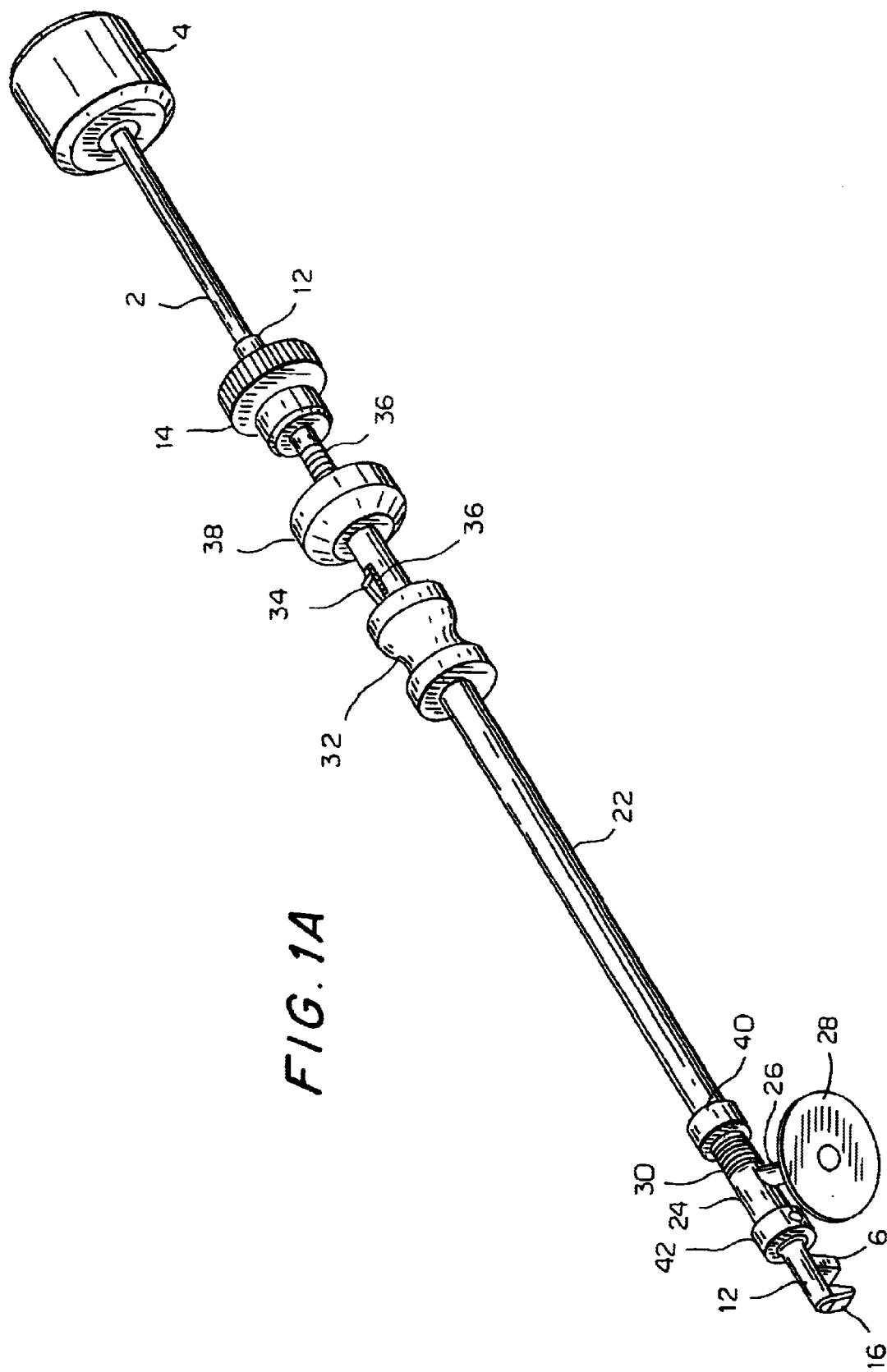
FIG. 1A is a perspective view of a first embodiment of a medical instrument according to the invention.

FIGS. 1A and 1B show a first embodiment of a surgical instrument incorporating the present invention. This instrument is composed of a tube, or rod, 2 connected at its proximal end to a first control element 4 and carrying at its distal end a first gripping jaw 6. The longitudinal axis of tube 2 defines the axis of the instrument. Jaw 6 is termed herein a hammer jaw. Tube 2 may be made of stainless steel The proximal end of tube 2 may be threaded for connection to a screw that fixes the axial position of control element 4 relative to tube 2 but allows tube 2 to rotate relative to control element 4. The distal end of tube 2 is connected to first control element 4 in such a manner that tube 2 moves axially together with element 4 but is able to rotate about its axis relative to element 4. First control element 4 is to be held in the palm of one hand by the operating surgeon during use.

Tube 2 slides in a sleeve 12 that carries at its distal end a second jaw 16, termed herein an anvil jaw. The proximal end of sleeve 12 is fixed to a second control element 14 that can be held in the same hand as control element 4 and can be moved by the thumb and index finger of the operating surgeon during use. By moving control elements 4 and 14 relative to one another along the axis of tube 2, tube 2 is moved relative to sleeve 12 to effect opening and closing of jaws 6 and 16. Jaw 6 is dimensioned to engage in sleeve 12 in a manner such that jaw 6 will not rotate relative to jaw 16 about the axis of the instrument. A similar arrangement is provided in my issued U.S. Pat. No. 6,221,083, the disclosure of which is incorporated herein by reference.

A further assembly is composed of a sleeve 22, a sleeve 24 that surrounds, and slides on, sleeve 22, an arm 26 fixed to sleeve 24, a pedestal, or disc, 28 fixed to arm 26, a compression spring 30 adjacent sleeve 24 and surrounding sleeve 22, a third control element 32 and a leaf spring 34 having a distal end that is fixed to sleeve 22 and a proximal end that is bent inwardly to bear against sleeve 12. The outer surface of sleeve 12 is provided with a succession of grooves 36. The inwardly bent proximal end of spring 34 engages in one of grooves 36. The inner peripheral surface of control element 32 bears against spring 34, as shown in FIG. 1B. Control element 32 can be shifted along the axis of the instrument relative to sleeve 22 to vary the radial inward deflection of spring 34. The greater the inward radial deflection, the higher the engagement force between the inwardly bent proximal end of spring 34 grooves 36 and therefore the higher the force needed to displace sleeve 22 relative to sleeve 12. Thus, the position of control element 32 along sleeve 22 in the axial direction determines the force needed to move sleeve 12 axially inside sleeves 22 and 24. After control element 32 has been brought to the desired position along sleeve 22, it is fixed in that position by a set screw. When the instrument is in use, control element 32 is fixed in position relative to sleeve 22. As sleeve 22 is displaced manually relative to sleeve 12, the inwardly bent proximal end of spring 34 moves from one groove 36 to the next. A fourth control element 38 is fixed to the proximal end of sleeve 22.

Sleeve 24 and spring 30 are interposed between two collets 40 and 42 that are both mounted on, and secured to, sleeve 22. The unit formed by sleeve 24, arm 26 and pedestal 28 can undergo limited axial movement relative to sleeve 22 while allowing that unit to rotate relative to sleeve 22. Spring 22 is in frictional contact with sleeve 24 and collet 40 and thus acts as a clutch that opposes, but does not prevent, rotation of that unit relative to sleeve 22. Before the instrument is placed into use, the initial position of sleeve 24 and the resistance to movement of sleeve 24 relative to sleeve 22 can be adjusted by varying the positions of collets 40 and 42 along sleeve 22. Then, collets 40 and 42 are fixed in place on sleeve 22 by tightening set screws provided in collets 40 and 42.

In use, pedestal 28 is placed on the organ that is undergoing a surgical procedure at a location where suturing is to be performed. Typically the organ would be the patient's heart, which is beating. Pedestal 28 is placed on the organ surface, and its position relative to jaws 6 and 16 can be adjusted by manually moving control element 38 relative control to element 4 in the axial direction. Pedestal 28 will follow movements of the organ and thus stabilize the position of jaws 6 and 16 relative to the organ, and particularly relative to the suturing site. Before or after positioning pedestal 28 on the organ surface, a suturing needle can be placed between jaws 6 and 16 and control element 14 can be moved axially relative to control element 4 to grip the needle between the jaws. After the distal end of the instrument has been placed at the suturing site, the needle can be manipulated, as by rotating control element 14 while holding control element 4 steady, to perform a suturing operation. During rotation of sleeve 12, pedestal 28 remains in position on the organ surface due to the ability of sleeve 24 to rotate relative to sleeve 22. Pedestal 28 allows jaws 6 and 16 to automatically follow movements of the suturing site without necessarily themselves being in contact with the organ surface. Thus, jaws 6 and 16 can be manipulated as needed while remaining in a stable position relative to the organ surface. Pedestal 28 can also be connected to arm 26 in a manner to be rotatable relative to arm 26, thereby enhancing the operating flexibility of the instrument.

FIGS. 2A, 2B, 2C and 2D show a second exemplary embodiment of the invention that is also in the form of a suturing instrument. Elements in FIGS. 2A–2D that are identical to elements in FIGS. 1A and 1B are given the same reference numerals. Thus, the distal end of the instrument includes hammer jaw 6 connected to a rod (element to in FIGS. 1A and 1B, not visible in FIGS. 2), and anvil jaw 16 carried by sleeve 12. Preferably, jaw 16 is integral with sleeve 12.

Also as in the embodiment of FIGS. 1, sleeve 12 is surrounded, adjacent its distal end, by the assembly that is composed of sleeve 24, arm 26, pedestal 28, spring 30 and collets 40 and 42, all of which cooperate and function in the manner described above with reference to FIGS. 1, except that here the assembly is mounted on sleeve 12 rather than a sleeve 22.

Sleeve 12 extends through circular passages provided in two discs 44 and 46, which may be made of Delrin®. Disc 44 is prevented from moving axially relative to sleeve 12 by two further collets 50 and 52 that are fixed to sleeve 12. However, sleeve 12 is allowed to rotate freely relative to disc 44. Sleeve 12 is also free to rotate relative to disc 46.

Proximally of disc 46, a spring 60 is mounted around sleeve 12. The distal end of spring 60 is held in place relative to sleeve 12 by a collet 62. The proximal end of spring 60 is secured to a collet 64 that is freely movable relative to sleeve 12. Collet 62 can be adjusted in position along sleeve 12 to provide the proper compressive stress in spring 60.

Sleeve 12 further extends through passages in two members 70 and 72, which may be made of stainless steel and which will be described in detail below. These passages are dimensioned to allow sleeve 12 to move freely parallel to its axis and to a limited extent transverse to its axis and to rotate about its axis. However, in order to cause tube 12 to rotate about its axis along with member 72, a special collet 74 is fixed to sleeve 12 and is provided with a finger 75 that extends into a slot in member 72, as shown most clearly in FIG. 2C.

The proximal end of sleeve 12 is secured to a collet 76 from which extends a tube 78. Collet 76 and tube 78 may be made of stainless steel and may be made in one piece.

All of the components described thus far, except for members 70 and 72, constitute a moving assembly, termed herein an armature, that is able to move axially and traversely with the organ that is undergoing a surgical procedure and that is in contact with pedestal 28.

One end of a flexible sheath 80 is fixed in tube 78. The other end of sheath 80 is fixed in a second tube 84 that is attached to, or integral with, a further collet 86. Collet 86 is secured to one end of a tube 90. The opposite end of tube 90 is fixed to member 72 with the aid of a set screw 92 (FIGS. 2C and 2D).

A nylon line, or metal, preferably stainless steel, cable, 94 is secured at one end to member 70 by a set screw 96. Cable 94 extends through tube 90, sheath 80 and a portion of sleeve 12. In sleeve 12, cable 94 is connected to an inner tube (not shown; corresponds in function to tube 2 of FIGS. 1)) that is fixed to, or integral with, jaw 6. That inner tube may extend proximally to near the proximal end of sleeve 12, where the inner tube may be secured to cable 94 by, for example, crimping, swaging, or cementing.

The armature further includes a tube 100 that contains a video camera and any optics needed to view jaws 6 and 16 and a region surrounding them. Tube 100 is fixed in bores in discs 44 and 46 and is held in place in discs 44 and 46 by suitable set screws (not shown). Since discs 44 and 46 are thus prevented from moving axially relative to sleeve 12, tube 100 will follow all axial and transverse movements of sleeve 12 but will not follow rotational movement of sleeve 12.

The armature is held in, and movable relative to, a housing assembly that includes a handle 110, a retaining element 112, a first tube 116 and a second tube 118 that surrounds the proximal end of tube 116. Retaining element 112 straddles tube 100 to prevent that tube, and discs 44 and 46, from following rotational movements of sleeve 12. Handle 110 and retaining element 112 may each be made of Delrin®. First tube 116 may be provided with a knurled or otherwise roughened portion 122 to facilitate manipulation of tube 116, as will be described in greater detail below.

Referring particularly to FIG. 2C, from which elements 110, 112 and 118 have been removed, member 70 is secured to first tube 116 by two screws 130 that engage in holes 132 in first tube 116. The heads of these screws will be flush with the outer surface of tube 116 so as to not interfere with sliding movement of tube 118 on tube 116. An axial slot 133 is provided in tube 116 between holes 132 for access to permit installation and adjustment of the position of cable 94. As shown in FIG. 2D, first tube 116 carries a screw 134 whose head protrudes into a slot in second tube 118. This screw allows tube 116 to slide axially relative to tube 118 while constraining tubes 116 and 118 to rotate as a unit.

Referring to FIGS. 2C and 2D, member 72 is secured to second tube 118 by two screws 136. As is apparent from FIG. 2D, tube 118 projects in the proximal direction beyond tube 116.

Figure 2B:
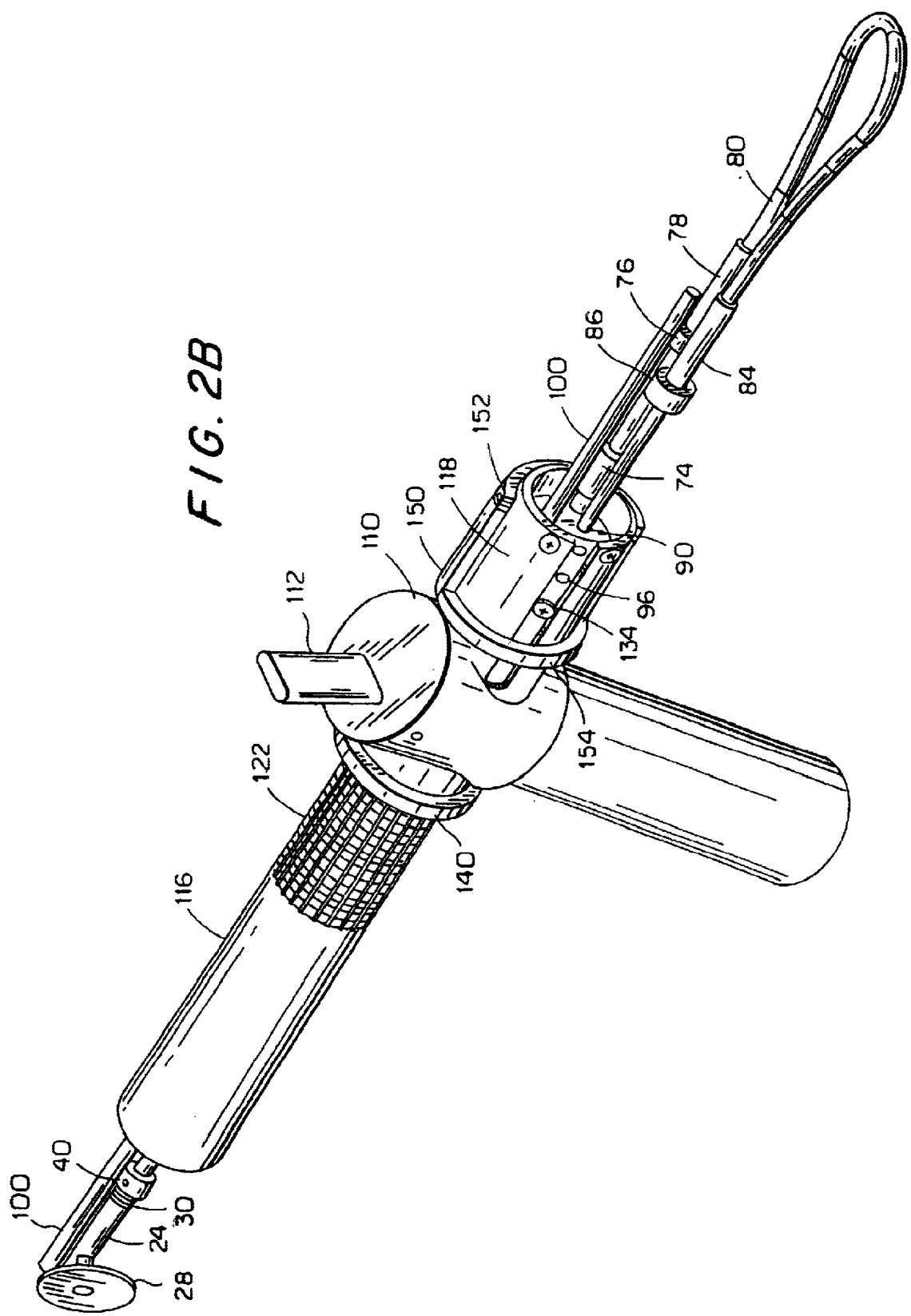
FIG. 2B is a second perspective view of the second embodiment
Figure 2E:
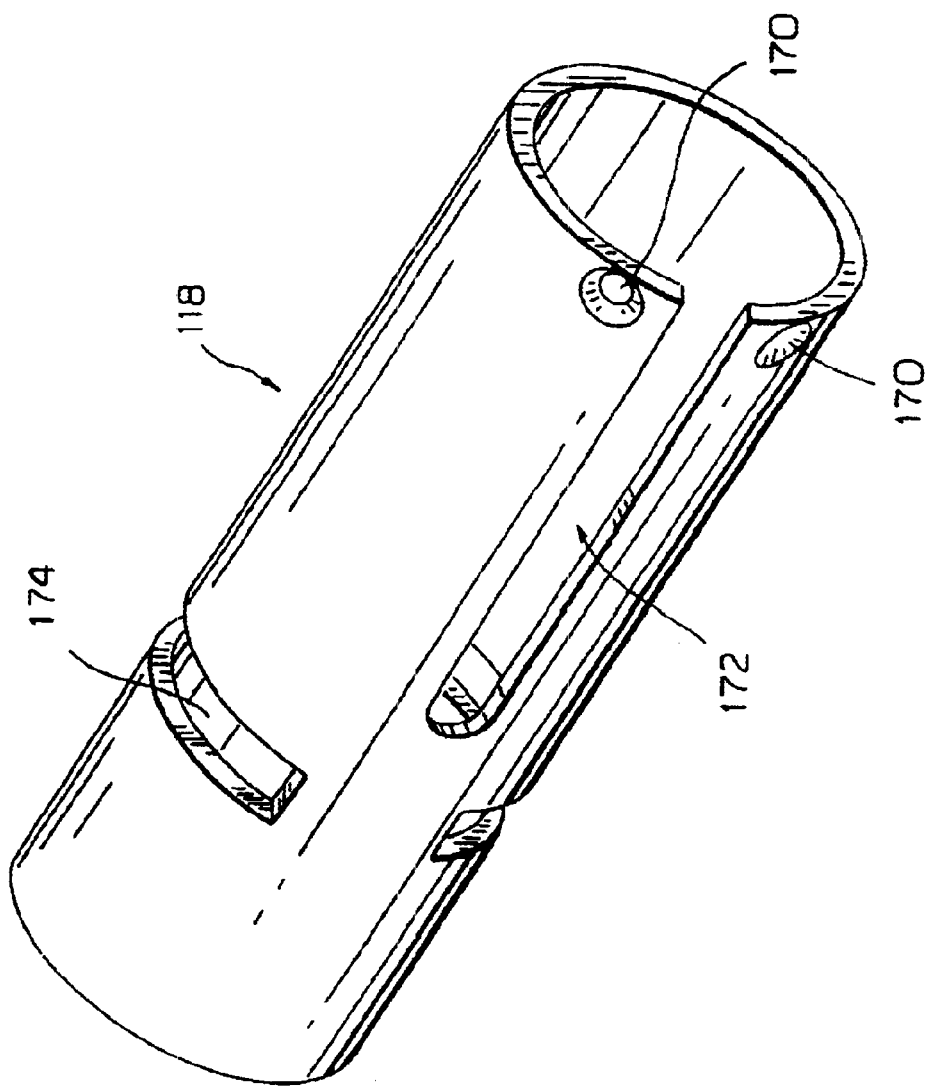
FIG. 2E is a perspective view of one component of the second embodiment.

As shown in FIGS. 2A, 2B and 2C, a ring 140 is secured to the distal end of tube 118 and bears against handle 110 to prevent axial movement of tube 118 relative to handle 110 in the proximal direction (to the right in FIG. 2B).

The instrument is completed by a sleeve 150 retained between two rings 152 and 154 on tube 118. Sleeve 150 is free to rotate relative to tube 118, but rings 152 and 154 are fixed to tube 118, as by set screws. Ring 154 bears against handle 110 to prevent axial movement of tube 118 relative to handle 110 in the distal direction. Sleeve 150 acts as a shield that prevents the operating physician's hand from touching tube 118 and hence from being rubbed by tube 118 when it is being rotated. If the operating physician's hand should touch sleeve 150 while tube 118 is being rotated, sleeve 150 will not rotate. Sleeve 150 may be made of a plastic such as Delrin®. The structure of tube 118 is shown most clearly in FIG. 2E. Tube 118 includes holes 170 for receiving screws 136, a longitudinal slot 172 that guides the head of screw 134 and a peripheral slot 174 through which retaining element 112 will extend. Slot 174 is dimensioned to permit the desire to tube 118.

In operation, the instrument is positioned in the manner described above in connection with the embodiments of FIGS. 1. However, in the embodiment of FIGS. 2, tube 116 is moved relative to handle 110 by gripping roughened area 122. Axial movement of tube 116 relative to tube 118 acts to open and close jaws 6 and 16. Rotation of tubes 116 and 118 as a unit acts to rotate sleeve 12 and jaws 6 and 16.

Tube 100 moves axially and transversely with sleeve 12 and the field of view of the associated video camera encompasses the region of action of jaws 6 and 16. However, tube 100 does not rotate with sleeve 12. Therefore, even though pedestal 28 is in contact with the body tissue being operated on and is moving therewith, the field of view of the video camera does not move relative to the region of action of jaws 6 and 16. As a result, the region of action of jaws 6 and 16 appears to be stationary in the image produced by the video camera.

Since the armature is movable axially and transversely relative to handle 110 and tube 116, and sleeve 12 is rotatable relative to handle 110, the handle and the operating physician's hand are isolated from the movements of the armature produced by the action of the body tissue on pedestal 28. In other words, when performing a procedure while viewing the image produced by the video camera in tube 100, the operating physician has the sensation, both tactilely and visually, that the body tissue is stationary even though, in the case of the heart, it is moving rhythmically. As a result, the procedure can be performed more quickly and with greater ease and accuracy.

FIGS. 3A and 3B show another form of construction for an assembly for supporting pedestal 28. This assembly includes a block 202 having a through bore (not shown) traversed by sleeve 12. Block 202 is disposed between collets 40 and 42, which are also mounted on sleeve 12, and compression spring 30 is interposed between collet 40 and block 202 to bias block 202 against collet 42.

Block 202 has a downwardly projecting portion provided with a second through bore (not shown) that extends at right angles to the first-mentioned through bore.

Two cylindrical members 210 and 212, each provided with a through bore, are disposed on opposite sides of the downwardly projecting portion of block 202. Block 202 has a recess to accommodate member 212. A compression spring 216 is interposed between member 212 and the downwardly projecting portion of block 202.

A pin, or rod, 220 extends through the through bores in members 210 and 212, the second through bore and spring 216 and these parts are held together with the aid of set screws in members 210 and 212 that are screwed down against pin 220.

Collets 40 and 42 can be shifted along sleeve 12 to adjust the position of pedestal 28 relative to jaws 6,16. In addition, the spacing between collets 40 and 42 can be varied to vary the force with which spring 30 presses against block 202. This determines the force needed to shift block 202, and thus pedestal 28, along the axis of tube 12 when the instrument is in use.

Pedestal 28 is secured to member 212 by a screw 224 that is screwed into a threaded bore in member 212 and secured to pedestal 28 by a set screw.

When collets 40 and 42 are brought to the desired positions along sleeve 12, set screws in those collets are tightened to secure the collets in position on sleeve 12.

Spring 30 is pressed against collet 42 and block 202 so that rotation of block 202 around sleeve 12 is opposed by the resulting friction forces, which can be varied by varying the spacing between collets 40 and 42.

Similarly, the spacing between member 212 and the downwardly projecting portion of block 202 can be varied, to vary the compression of spring 216, by adjusting the position of member 212 relative to pin 220. Rotation of member 212 and pedestal 28 about the axis of pin 220 is opposed by the resulting friction forces between spring 216 and both member 212 and the downwardly projecting portion of block 202.

Thus, both springs 30 and 216 act as clutches.

Thus arrangement allows pedestal 28 to lie flat against the surface of the body tissue when the instrument is tilted about the axis of pin 220.

While the embodiments illustrated herein are equipped with jaws for gripping a suture needle or other item, these embodiments can be constructed with other tools, such as a stapler that will be operated in much the same manner as described above. The jaws could also be replaced by forceps that can be used to rotate the wall of an artery to the most favorable orientation for suturing.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. A medical instrument for performing a procedure on body tissue, comprising:
    an elongated tool carrier member a longitudinal axis and having a distal end;
    an operating tool mounted at said distal end;
    operating means coupled to said carrier member and said tool for allowing manual operation of said tool; and
    a stabilizing member carried by said carrier member and including a plate element laterally offset from said longitudinal disposed to bear against the body tissue in order to cause said tool to follow movement of the body tissue.

2. The medical instrument of claim 1 wherein said operating means include a handle and a mechanism for controlling operation of said tool.

3. The medical instrument of claim 2 wherein said tool carrier is movable relative to said handle.

4. The medical instrument of claim 3 wherein said tool carrier has a longitudinal axis and said stabilizing member is rotatable relative to said tool carrier about said axis.

5. The medical instrument of claim 4 wherein said stabilizing member is movable over a limited range relative to said tool carrier parallel to said axis of said tool carrier.

6. The medical instrument of claim 4 wherein said mechanism for controlling operation of said tool comprises:

a first tube that is rotatable relative to said handle about an axis and movable in translation relative to said handle; and coupling elements coupling said tube to said tool carrier and said tool for causing said tool carrier and said tube to rotate about said longitudinal axis of said tool carrier in response to rotation of said tube and for operating said tool in response to movement of said tube in translation relative to said handle.

7. The medical instrument of claim 6 wherein said coupling elements comprise a second tube that is mounted for rotation with said first tube and is prevented from movement in translation relative to said handle.

8. The medical instrument of claim 7 wherein said observation device comprises a video camera.

9. The medical instrument of claim 6 wherein said tool carrier is rotatable about said axis and said observation device is mounted to not rotate with said tool carrier.

10. The medical instrument of claim 3, further comprising an observation device having a field of view that encompasses said tool, said observation device being mounted for movement with said tool carrier in directions parallel and transverse to said axis.

11. A method for performing a procedure on a body organ that is moving using the medical instrument of claim 1, comprising:

positioning the instrument so that the plate element of the stabilizing member contacts the organ at a location where the procedure is to be performed; and manually manipulating the operating means in order to perform the procedure while maintaining the plate element of the stabilizing member in contact with the organ.

* * * * *